(12) United States Patent
Higgins et al.

(10) Patent No.: US 12,004,936 B2
(45) Date of Patent: Jun. 11, 2024

(54) INCONTINENCE CLAMP DEVICE

(71) Applicants: Shawn P Higgins, Cheyenne, WY (US); Ignacio Navarro De Corcuera, Madrid (ES)

(72) Inventors: Shawn P Higgins, Cheyenne, WY (US); Ignacio Navarro De Corcuera, Madrid (ES)

(73) Assignee: Cross Innovations, LLC, Cheyenne, WY (US)

( * ) Notice: Subject to any disclaimer, the term of this patent is extended or adjusted under 35 U.S.C. 154(b) by 821 days.

(21) Appl. No.: 17/063,804

(22) Filed: Oct. 6, 2020

(65) Prior Publication Data
US 2021/0015594 A1   Jan. 21, 2021

(51) Int. Cl.
*A61F 2/00* (2006.01)
(52) U.S. Cl.
CPC .................... *A61F 2/0054* (2013.01)
(58) Field of Classification Search
CPC .... A61F 2/0054; A61F 2/0045; A61F 2/0031; A61F 2/0018; A61F 2/0013; A61F 2/0009; A61F 2/0004; A61F 2/00
See application file for complete search history.

(56) References Cited

U.S. PATENT DOCUMENTS

| | | | | |
|---|---|---|---|---|
| 5,571,125 A * | 11/1996 | Chadwick | ............ | A61B 17/122 606/151 |
| 6,131,576 A * | 10/2000 | Davis | .................... | A61F 2/0054 128/885 |
| 7,107,995 B2 * | 9/2006 | Parkes | ...................... | A61F 5/41 600/38 |
| 10,624,728 B2 * | 4/2020 | Velez Wiesner | ...... | A61F 2/0054 |
| 2004/0129277 A1 * | 7/2004 | Parkes | .................. | A61F 2/0054 128/885 |
| 2008/0121241 A1 * | 5/2008 | Dennis | .................. | A61F 2/0054 128/885 |
| 2019/0269489 A1 * | 9/2019 | Kuenzel | ............... | A61F 2/0054 |
| 2020/0197146 A1 * | 6/2020 | Velez Wiesner | ...... | A61F 2/0054 |
| 2021/0338404 A1 * | 11/2021 | Velez Wiesner | ...... | A61F 2/0054 |

FOREIGN PATENT DOCUMENTS

WO    WO-2019063994 A1 *   4/2019

* cited by examiner

*Primary Examiner* — Tarla R Patel
(74) *Attorney, Agent, or Firm* — Dan B Law PLLC; Daniel S. Bretzius

(57) ABSTRACT

An incontinence clamping device has been presented herein. The incontinence clamping device comprises an upper clamp arm having a stopper and a bottom clamp arm having a locking component with a plurality of interlocking gaps. The incontinence clamping device further comprises a top and a bottom stabilizer having a plurality of zig-zag portion including at least one or more elevated and one or more non-elevated portions. The incontinence clamping device further comprises an upper silicone fitting that is used for accommodating the top stabilizer and a bottom silicone fitting that is used for accommodating the bottom stabilizer. The incontinence clamping device in its closed state allows for delivery of different pressures to urethra and corpus spongiosum as a function of various sizes of penises in a flaccid state.

3 Claims, 13 Drawing Sheets

FIG. 4C  FIG. 4B

INCONTINENCE CLAMP DEVICE

FIELD OF THE INVENTION

The present disclosure generally relates to a clamping device, and more particularly to an easily adjustable and flexible incontinence clamping device that can be used for restricting the flow of urine through the penis of a human male and providing for the voluntary release of urine.

BACKGROUND

Incontinence is the uncontrolled and undesired passage of urine and is generally considered as a problem faced by many men and, especially, older men. Incontinence may be caused by, for example, medical operations, partial or full sphincter loss, disease, neurological dysfunction, malformation of the urethral valve, and physical deterioration accompanying advancing age such that the natural urethral valve or sphincter is no longer capable of controlling the flow of urine from the bladder. Whatever the cause, incontinence is a significant problem resulting in distress, embarrassment, inconvenience, and restriction of activities. To date, the common means of preventing the involuntary flow of urine in incontinent males has been to clamp the penis via a device. However, the use of such conventional device generally becomes painful, socially restrictive, and difficult to keep clean. Such devices cause pressure to be applied upon the urethra, which consequently restricts the flow of urine through the penis.

U.S. Pat. No. 7,107,995 (entitled "Urinary-control device") discloses a urinary-control device for inhibiting male incontinence includes an upper clamping member; a lower clamping member; a hinge; and a releasable, self-locking mechanism. The upper clamping member has first and second distal ends and a substantially arcuate inner surface extending therebetween. The inner surface is adapted to be disposed about a portion of a penis. The lower clamping member has first and second distal ends and a substantially arcuate inner surface extending therebetween. The inner surface is adapted to be disposed about a portion of the penis and opposite the upper clamping member. The hinge is defined at the first distal ends for allowing articulated movement of the upper and lower clamping members relative to one another. The self-locking mechanism is defined at the second distal ends opposite the hinge and adapted to adjustably lock the second distal ends together, thereby mounting the device to the penis. The lower clamping member includes a removable pressure mechanism mounted on the inner surface of the lower clamping member and between the distal ends thereof so as to be located generally opposite the urethra of the penis. The removable pressure mechanism extends in a direction toward the inner surface of the upper clamping member so as to collapse the urethra in such a manner as to inhibit flow of urine therethrough when the device is mounted to the penis.

U.S. patent Ser. No. 10/624,728 (entitled "External male incontinence clamp") discloses an incontinence clamp includes an upper clamp arm and a lower clamp arm. Each of the upper and lower clamp arms include a first end, a second end, an inner surface, and an outer surface. The inner surfaces face each other. A hinge pivotally connects the first ends of the upper and lower clamp arms together. An upper guide is coupled to the inner surface of the upper clamp arm and a lower guide is coupled to the inner surface of the lower clamp arm. A connector releasably connects the second ends of the upper clamp arm and the lower clamp arm together.

The foregoing approaches to alleviating the problem of urinary incontinence in men leave much to be desired, since these designs offer little in the way of comfort or convenience for the user. In addition, none of these clamps is capable of adjusting pressure upon the urethra. It should be obvious to the casual observer that such devices are neither comfortable nor efficient in resolving the problems imposed by an incontinent condition. Thus, there is a need for an improved penile clamp that is safe, comfortable, easily cleanable, and more socially practical (i.e., utilizing one-handed operation) than that heretofore devised.

SUMMARY

It will be understood that this disclosure is not limited to the particular incontinence clamping device described herein, as there can be multiple possible embodiments of the present disclosure which are not expressly illustrated in the present disclosure. It is also to be understood that the terminology used in the description is for the purpose of describing the particular versions or embodiments only and is not intended to limit the scope of the present disclosure.

It is an objective of the present invention to provide an incontinence clamping device that prevents or substantially reduces leakage from the urethra of penises of various sizes. The incontinence clamping device should allow for delivery of different pressures to the urethra and the corpus spongiosum as a function of various sizes of penises in a flaccid state. The incontinence clamping device uses variable adjustment to enable application of different pressures to the urethra and the corpus spongiosum to accommodate needs of individual users. The incontinence clamping device is further designed to permit blood flow through the penis while preventing or substantially reducing leakage from the urethra. The incontinence clamping device of the present invention employs a quick-release mechanism for easy positioning on the penile shaft and removal therefrom for urination and is more convenient and easier to attach, remove, and use than such devices known in the related art. The incontinence clamping device of the present invention is lightweight. The incontinence clamping device of the present invention uses variable adjustment to enable application of different pressures to the penis to accommodate needs of individual users. The incontinence clamping device of the present invention does not inflict pain, trauma, and/or damage to the skin and underlying tissues of the penile shaft. The incontinence clamping device of the present invention is more comfortably worn by the user than such devices known in the related art and, thus, gives the user more confidence and freedom of movement. The incontinence clamping device of the present invention is compact in design and, thus, unobtrusive. The incontinence clamping device of the present invention is simple and inexpensive to construct. The incontinence clamping device of the present invention can be easily cleaned so that it remains sanitary.

These and other features and advantages of the present invention will become apparent from the detailed description below, in light of the accompanying drawings.

BRIEF DESCRIPTION OF ACCOMPANYING DRAWINGS

The present invention is illustratively shown and described in reference to the accompanying drawings, in which:

FIG. 4B is a diagram that illustrates a second perspective view of the top stabilizer of the incontinence clamping device, according to an exemplary embodiment of the present invention;

FIG. 4C is a diagram that illustrates a cross-sectional side view of the top stabilizer of the incontinence clamping device, according to an exemplary embodiment of the present invention;

DETAILED DESCRIPTION

Figure 1:
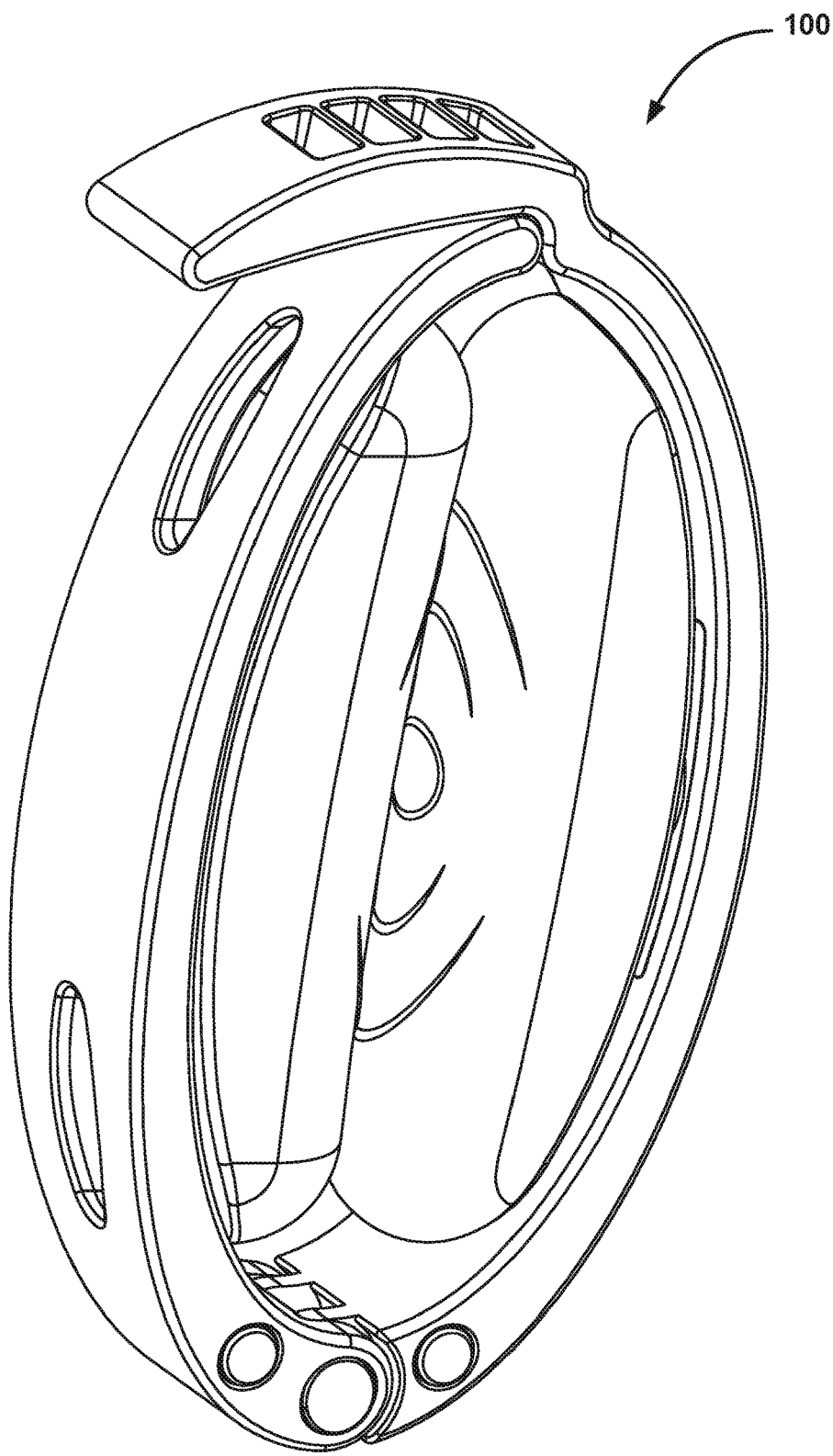
FIG. 1 is a diagram that illustrates a perspective view of an incontinence clamping device, according to an exemplary embodiment of the present invention.

As used in the specification and claims, the singular forms "a", "an", and "the" may also include plural references. For example, the term "an article" may include a plurality of articles. Those with ordinary skill in the art will appreciate that the elements in the figures are illustrated for simplicity and clarity and are not necessarily drawn to scale. For example, the dimensions of some of the elements in the figures may be exaggerated, relative to other elements, to improve the understanding of the present invention. There may be additional components described in the foregoing application that are not depicted on one of the described drawings. In the event such a component is described, but not depicted in a drawing, the absence of such a drawing should not be considered as an omission of such design from the specification.

Before describing the present invention in detail, it should be observed that the present invention utilizes a combination of components, which constitutes a unique design of an easily adjustable and flexible incontinence clamping device. This device can be used for restricting the flow of urine through the penis of a human male and providing for the voluntary release of urine. Accordingly, the components have been represented, showing only specific details that are pertinent for an understanding of the present invention so as not to obscure the disclosure with details that will be readily apparent to those with ordinary skill in the art having the benefit of the description herein. As required, the detailed embodiments of the present invention are disclosed herein. However, it is to be understood that the disclosed embodiments are merely exemplary of the present invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the present invention.

References to terms "one embodiment", "an embodiment", "another embodiment", "yet another embodiment", "one example", "an example", "another example", "yet another example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment. The words "comprising", "having", "containing", and "including", and other forms thereof, are intended to be equivalent in meaning and be open ended in that an item or items following any one of these words is not meant to be an exhaustive listing of such item or items or meant to be limited to only the listed item or items.

Unless stated otherwise, terms such as "first" and "second" are used to arbitrarily distinguish between the elements or entities. Thus, these terms are not necessarily intended to indicate temporal or other prioritization of such elements or priorities. While various exemplary embodiments of the disclosed incontinence clamping device have been described below, a person having ordinary skills in the art would understand that the incontinence clamping device have been presented for purposes of example only, and not limitations. It is not exhaustive and does not limit the present invention to the precise form disclosed. Modifications and variations of the disclosed incontinence clamping device are possible considering the below teachings or may be acquired from practicing of the present invention, without departing from the breadth or scope.

The incontinence clamping device of the present invention will now be described with reference to the accompanying drawings, particularly with respect to FIGS. 1-13.

FIG. 1 is a diagram that illustrates a perspective view of an incontinence clamping device 100, according to an exemplary embodiment of the present invention. The incontinence clamping device 100 may be configured to allow for delivery of different pressures to the urethra and the corpus spongiosum as a function of various sizes of penises in a flaccid state. The incontinence clamping device 100 comprises a variable adjustment component that is configured to enable application of different pressures to the urethra and the corpus spongiosum to accommodate needs of individual users. The incontinence clamping device 100 has been designed to permit blood flow through the penis while preventing or substantially reducing leakage from the urethra. The incontinence clamping device 100 employs a quick-release mechanism that may be utilized for easy positioning on the penile shaft and removal therefrom for urination and is more convenient and easier to attach, remove, and use. The incontinence clamping device 100 is a lightweight and compact in design and, thus, unobtrusive. The incontinence clamping device 100 uses variable adjustment to enable application of different pressures to the penis to accommodate needs of individual users. The incontinence clamping device 100 does not inflict pain, trauma, and/or damage to the skin and underlying tissues of the penile shaft. The incontinence clamping device 100 has been designed to be worn more comfortably by the user and, thus, gives the user more confidence and freedom of movement. Various components of the incontinence clamping device 100 will now be described below in conjunction with FIGS. 2-13.

Figure 2A:
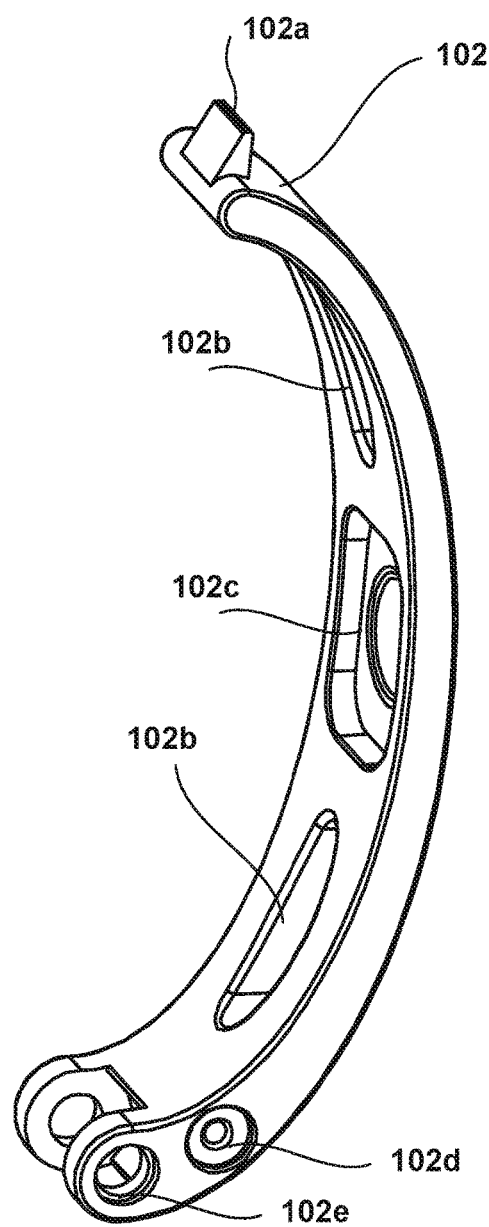
FIG. 2A is a diagram that illustrates a first perspective view of an upper clamp arm of the incontinence clamping device, according to an exemplary embodiment of the present invention.
Figure 2B:
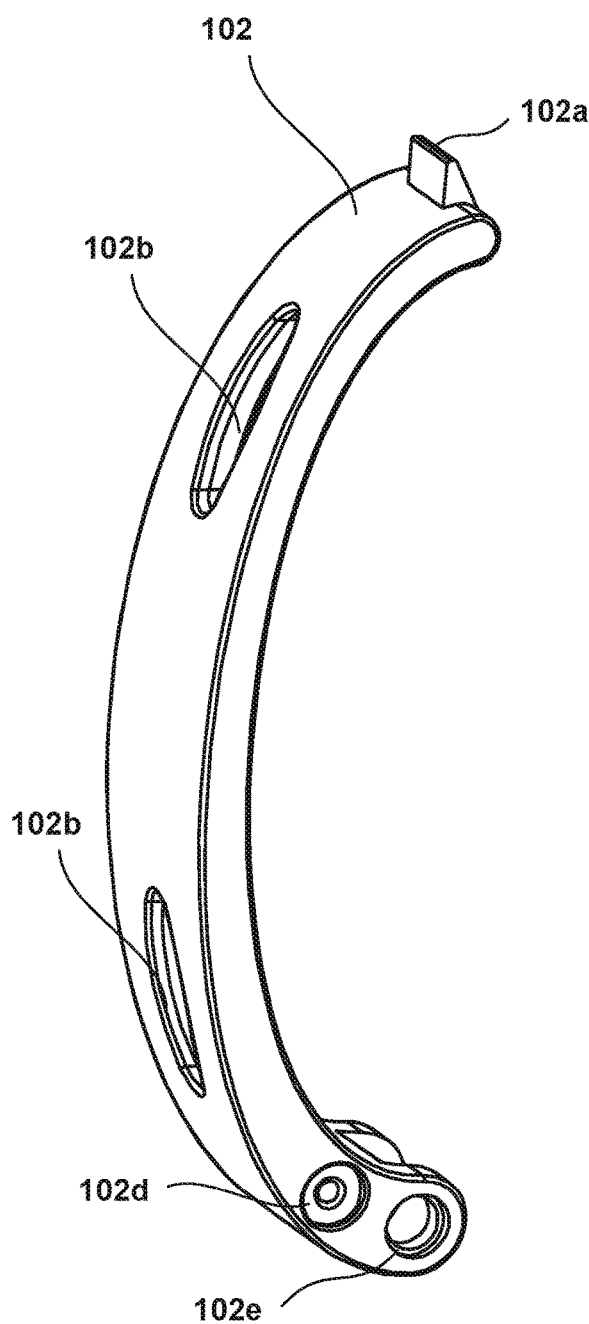
FIG. 2B is a diagram that illustrates a second perspective view of the upper clamp arm of the incontinence clamping device, according to an exemplary embodiment of the present invention.

FIG. 2A is a diagram that illustrates a first perspective view of an upper clamp arm 102 of the incontinence clamping device 100, according to an exemplary embodiment of the present invention. In FIG. 2A, the first perspective view of the upper clamp arm 102 has been shown from inside. FIG. 2B is a diagram that illustrates a second perspective view of the upper clamp arm 102 of the incontinence clamping device 100, according to an exemplary embodiment of the present invention. In FIG. 2B, the second perspective view of the upper clamp arm 102 has been shown from outside.

In an embodiment, the upper clamp arm 102 comprises a stopper 102a, a plurality of gaps 102b (that can be seen from inside as well as outside as shown in FIGS. 2A and 2B), and a locking segment 102c (that can be seen only from inside as shown in FIG. 2A and is not visible from outside). The locking segment 102c may be used for facilitating a locking mechanism with a lock ring (as described later in conjunction with FIGS. 7A and 7B). The upper clamp arm 102 further comprises a plug-in hole 102d and a plug-in hole 102e. These holes are used for plugging one or more plastic stoppers or screws while connecting the upper clamp arm 102 to a bottom clamp arm (shown in FIGS. 3A and 3B).

Figures 3A, 3B:
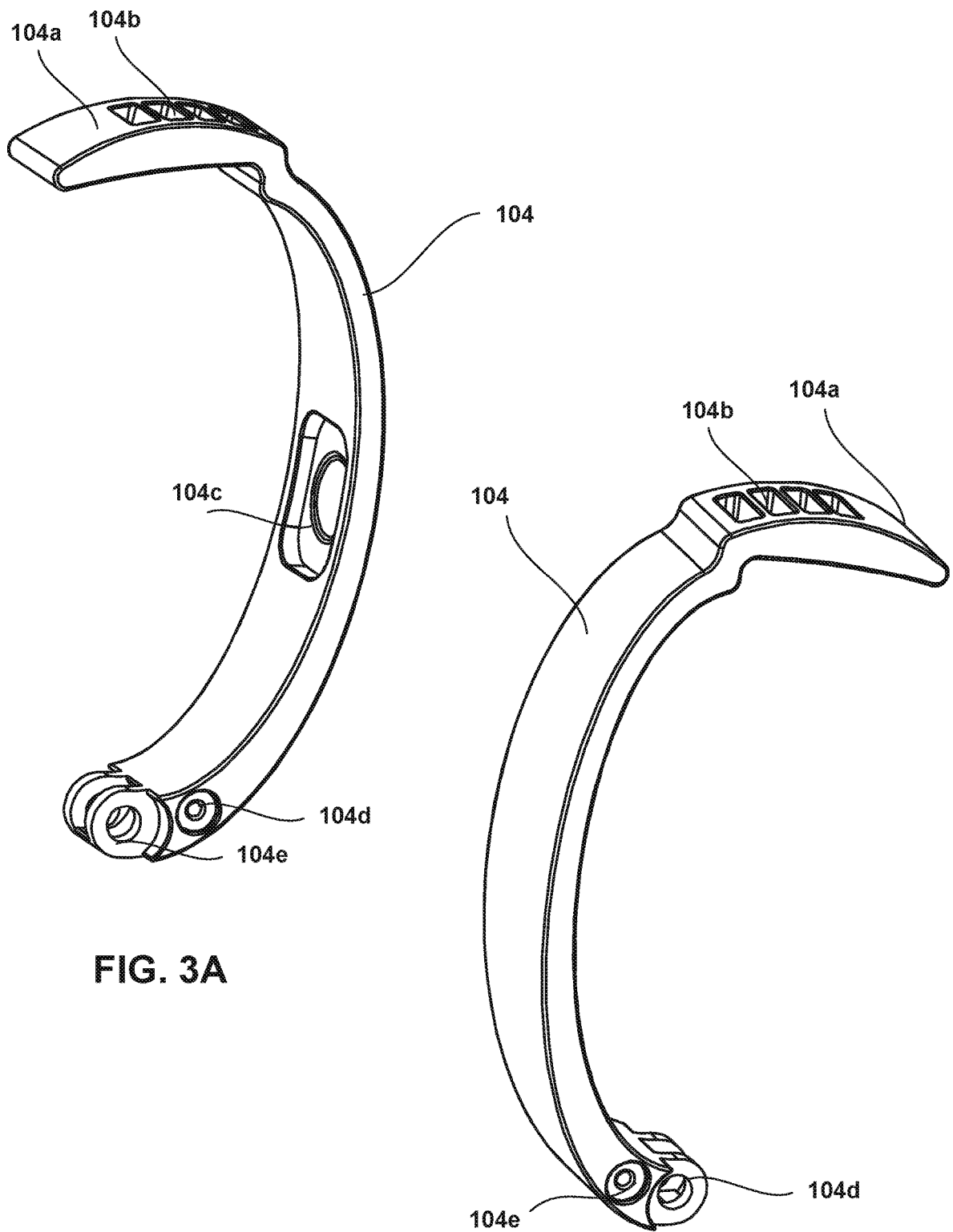
FIG. 3A is a diagram that illustrates a first perspective view of a bottom clamp arm of the incontinence clamping device, according to an exemplary embodiment of the present invention.
FIG. 3B is a diagram that illustrates a second perspective view of the bottom clamp arm of the incontinence clamping device, according to an exemplary embodiment of the present invention.

In an embodiment, the upper clamp arm 102 may be made up of a polycarbonate material. The stopper 102a may be a hook or hinge or interlocking tooth that is attached to an edge of the upper clamp arm 102 as shown in FIGS. 2A and 2B. The stopper 102a may be made up of a polycarbonate material. The stopper 102a may be secured in between a plurality of interlocking gaps, releasably connecting the one or more ends together. As illustrated in the Figures, the stopper 102a may protrude from the outer surface of the upper clamp arm 102. The plurality of interlocking gaps may protrude from a surface extending from one end of the bottom clamp arm as shown in FIGS. 3A and 3B. Pressing the clamp arms together releasably retains the second end of the upper clamp arm 102 to the second end of the bottom clamp arm. The stopper 102a disposed in between different interlocking gaps adjusts the diameter of the incontinence clamping device 100.

FIG. 3A is a diagram that illustrates a first perspective view of a bottom clamp arm 104 of the incontinence clamping device 100, according to an exemplary embodiment of the present invention. In FIG. 3A, the first perspective view of the bottom clamp arm 104 has been shown from inside. FIG. 3B is a diagram that illustrates a second perspective view of the bottom clamp arm 104 of the incontinence clamping device 100, according to an exemplary embodiment of the present invention. In FIG. 3B, the second perspective view of the bottom clamp arm 104 has been shown from outside. In an embodiment, the bottom clamp arm 104 may be made up of a polycarbonate material.

In an embodiment, the bottom clamp arm 104 comprises a device locking component 104a that includes the plurality of interlocking gaps 104b. These gaps 104b can be used along with the stopper 102a to facilitate the locking of the upper clamp arm 102 and the bottom clamp arm 104 of the incontinence clamping device 100. One of the gaps 104b may be selected to adjust the size of the incontinence clamping device 100. During the locking, the stopper 102a removably engages with one of the gaps 104b, thereby securing the upper clamp arm 102 with the bottom clamp arm 104 of the incontinence clamping device 100.

In an embodiment, the bottom clamp arm 104 further comprises a locking segment 104c (that can be seen only from inside as shown in FIG. 3A and is not visible from outside). The locking segment 104c may be used for facilitating a locking mechanism with a lock ring (as described later in conjunction with FIGS. 7A and 7B). Basically, the lock ring fits into the locking segment 104c from inside of the bottom clamp arm 104. The bottom clamp arm 104 further comprises a plug-in hole 104d and a plug-in hole 104e. These holes are used for plugging one or more plastic stoppers or screws while connecting the upper clamp arm 102 to the bottom clamp arm 104.

Figure 4A:
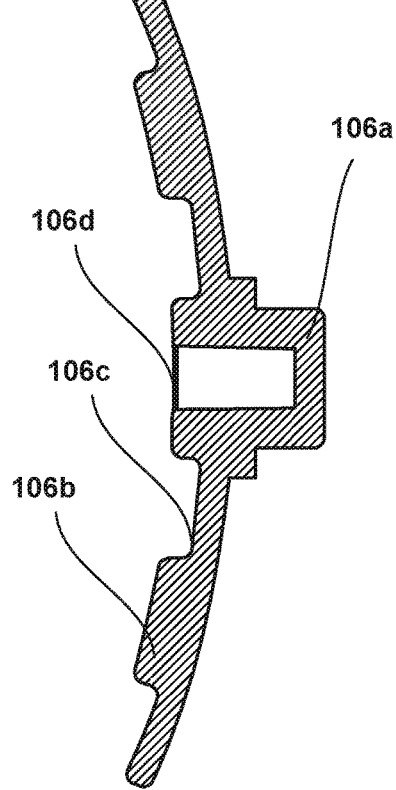
FIG. 4A is a diagram that illustrates a first perspective view of a top stabilizer of the incontinence clamping device, according to an exemplary embodiment of the present invention.
Figure 4A:
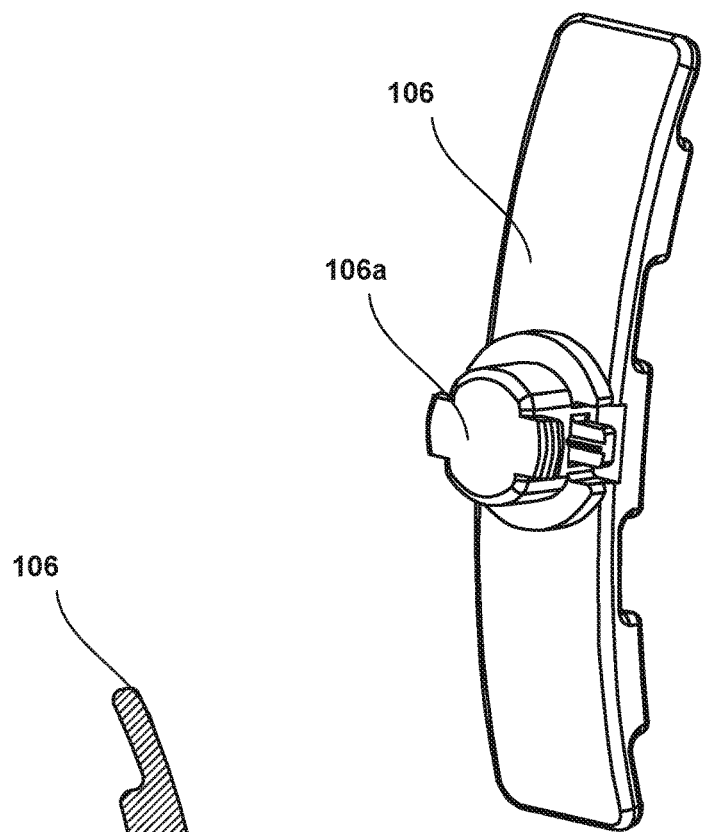
Figure 4A:
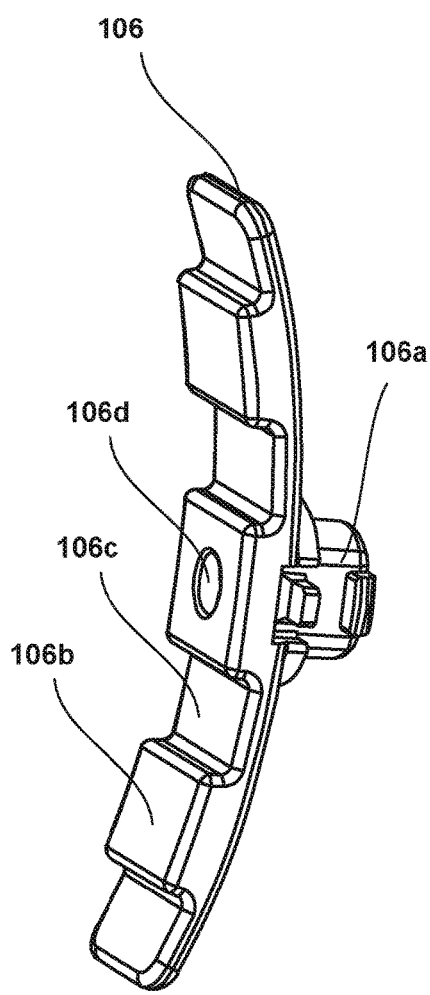

FIG. 4A is a diagram that illustrates a first perspective view of a top stabilizer 106 of the incontinence clamping device 100, according to an exemplary embodiment of the present invention. In FIG. 4A, the first perspective view of the top stabilizer 106 has been shown from outside showing an outer surface. FIG. 4B is a diagram that illustrates a second perspective view of the top stabilizer 106 of the incontinence clamping device 100, according to an exemplary embodiment of the present invention. In FIG. 4B, the second perspective view of the top stabilizer 106 has been shown from inside showing an inner surface. FIG. 4C is a diagram that illustrates a cross-sectional side view of the top stabilizer 106 of the incontinence clamping device 100, according to an exemplary embodiment of the present invention. In an embodiment, the top stabilizer 106 may be made up of a polycarbonate material.

In an embodiment, the top stabilizer 106 may comprise a lock 106a (provided on the outer surface) that is configured to get locked with the lock ring of the upper clamp arm 102. In one embodiment, the lock 106a may be manually placed into the lock ring and then may be manually rotated in one direction (for example, in a clockwise direction) to complete the locking of the lock 106a with the lock ring of the upper clamp arm 102. Similarly, to perform unlocking, the lock 106a may be manually rotated in the opposite direction (for example, in an anti-clockwise direction) to unlock the lock 106a from the lock ring of the upper clamp arm 102. In another embodiment, the lock 106a may be a toggle lock and may include a mechanical button that can be operated to lock or unlock the lock 106a into or out of the lock ring of the upper clamp arm 102.

In an embodiment, the top stabilizer 106 may further comprise the inner surface having a plurality of zig-zag portions (as shown by 106b and 106c) including one or more elevated portions 106b and non-elevated portions 106c. Further, the central elevated portion may include a circular gap or hole 106d. The elevated portions 106b and the non-elevated portions 106c may be adjacent to each other. Each of the elevated portions 106b or the non-elevated portions 106c may be square or rectangular in shape as shown.

Figure 5A:
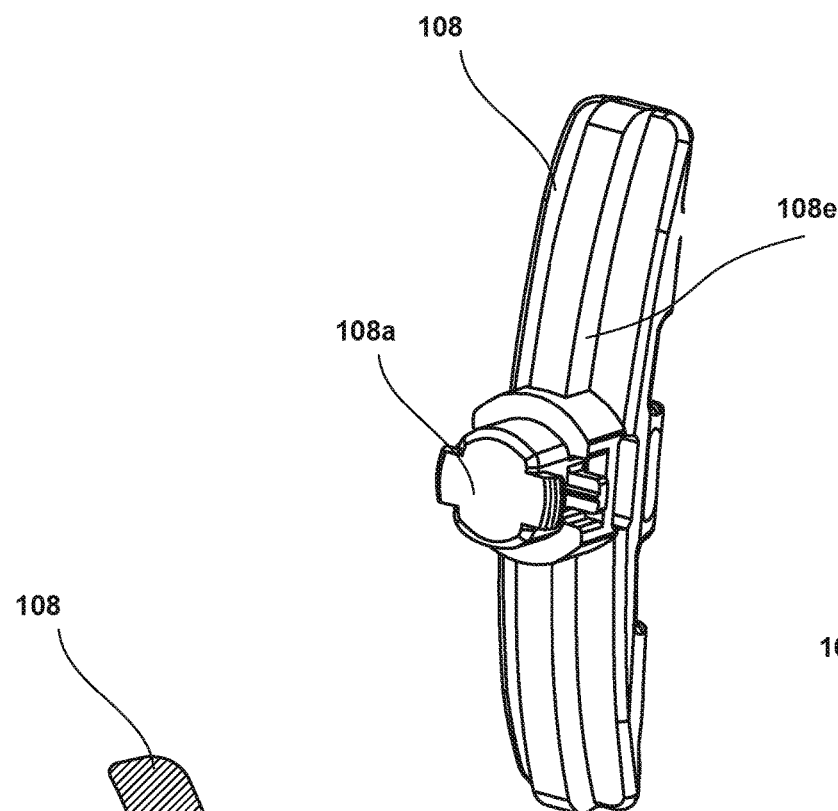
FIG. 5A is a diagram that illustrates a first perspective view of a bottom stabilizer of the incontinence clamping device, according to an exemplary embodiment of the present invention.
Figure 5C:
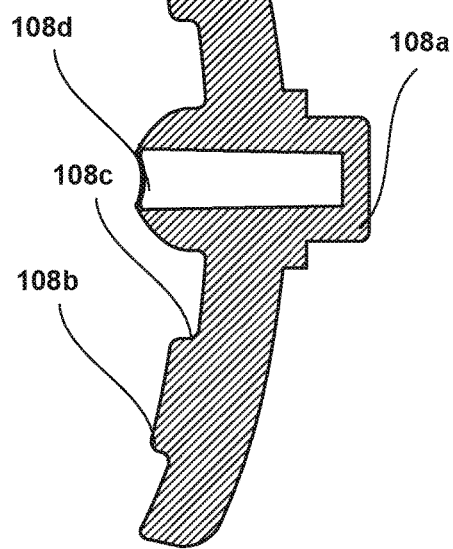
FIG. 5C is a diagram that illustrates a cross-sectional side view of the bottom stabilizer of the incontinence clamping device, according to an exemplary embodiment of the present invention.
Figure 5B:
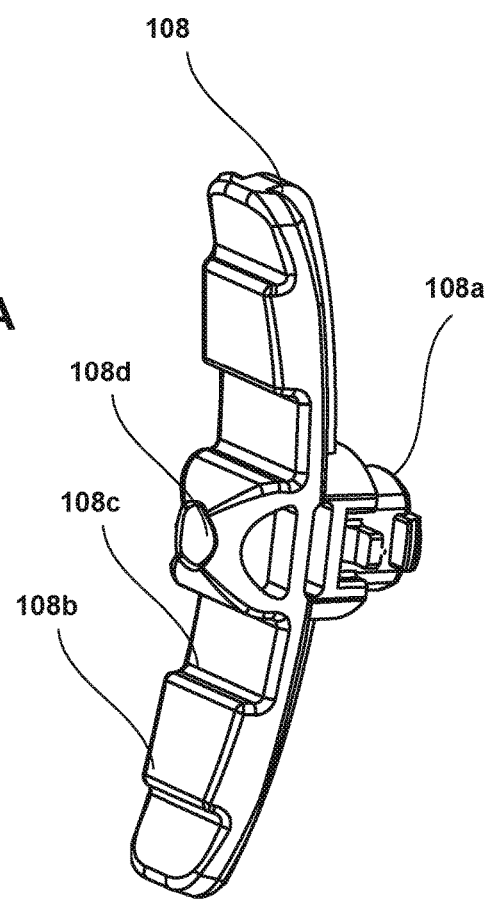
FIG. 5B is a diagram that illustrates a second perspective view of the bottom stabilizer of the incontinence clamping device, according to an exemplary embodiment of the present invention.

FIG. 5A is a diagram that illustrates a first perspective view of a bottom stabilizer 108 of the incontinence clamping device 100, according to an exemplary embodiment of the present invention. In FIG. 5A, the first perspective view of the bottom stabilizer 108 has been shown from outside showing an outer surface. FIG. 5B is a diagram that illustrates a second perspective view of the bottom stabilizer 108 of the incontinence clamping device 100, according to an exemplary embodiment of the present invention. In FIG. 5B, the second perspective view of the bottom stabilizer 106 has been shown from inside showing an inner surface. FIG. 5C is a diagram that illustrates a cross-sectional side view of the bottom stabilizer 108 of the incontinence clamping device 100, according to an exemplary embodiment of the present invention. In an embodiment, the bottom stabilizer 108 may be made up of a polycarbonate material.

In an embodiment, the bottom stabilizer 108 may comprise a lock 108a (provided on the outer surface) that is configured to get locked with the lock ring of the bottom clamp arm 104. In one embodiment, the lock 108a may be manually placed into the lock ring and then may be manually rotated in one direction (for example, in a clockwise direction) to complete the locking of the lock 108a with the lock ring of the bottom clamp arm 104. Similarly, to perform unlocking, the lock 108a may be manually rotated in the opposite direction (for example, in an anti-clockwise direction) to unlock the lock 108a from the lock ring of the bottom clamp arm 104. In another embodiment, the lock 108a may be a toggle lock and may include a mechanical button that can be operated to lock or unlock the lock 108a into or out of the lock ring of the bottom clamp arm 102.

In an embodiment, the bottom stabilizer 108 may further comprise the inner surface having a plurality of zig-zag portions (as shown by 108b and 108c) including one or more elevated portions 108b and non-elevated portions 108c. Further, the central elevated portion may include a circular gap or hole 108d. The elevated portions 108b and the non-elevated portions 108c may be adjacent to each other. Each of the elevated portions 108b or the non-elevated portions 108c may be square or rectangular in shape as shown. However, the central elevated portion is like a diamond or crown shaped portion having the circular gap or hole 108d at its center as shown. The bottom stabilizer 108 may further comprise an elevated portion 108e on its outer surface as shown.

Figure 6A:
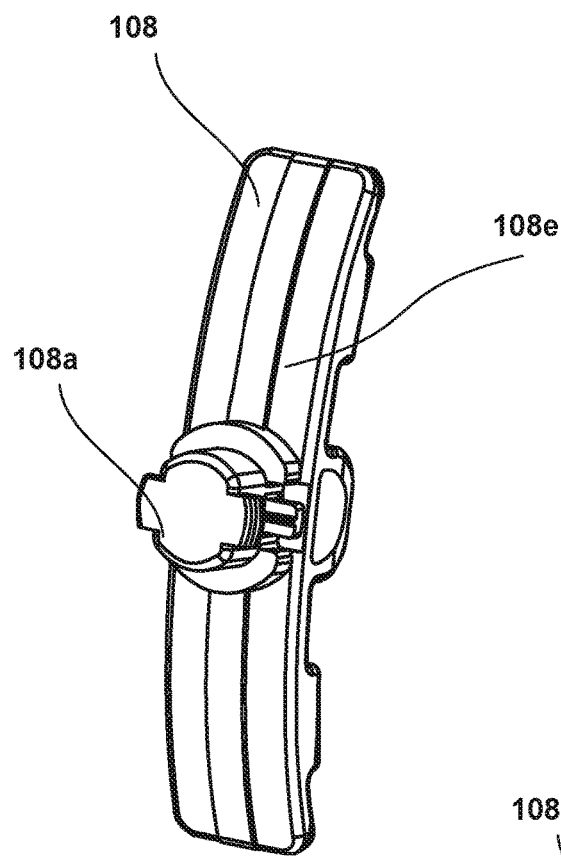
FIG. 6A is a diagram that illustrates a first perspective view of a bottom stabilizer of the incontinence clamping device, according to another exemplary embodiment of the present invention.
Figure 6C:
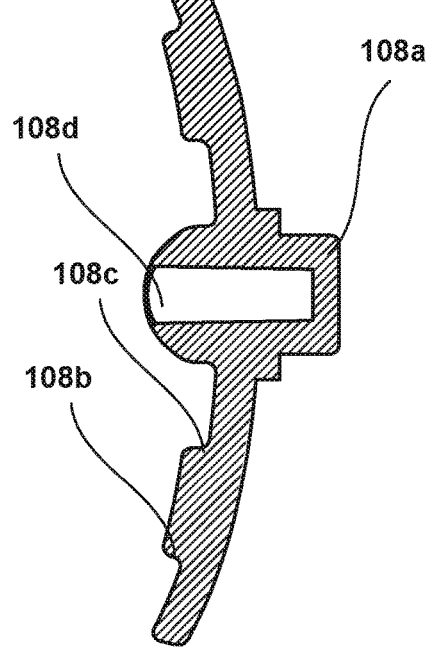
FIG. 6C is a diagram that illustrates a cross-sectional side view of the bottom stabilizer of the incontinence clamping device, according to another exemplary embodiment of the present invention.
Figure 6B:
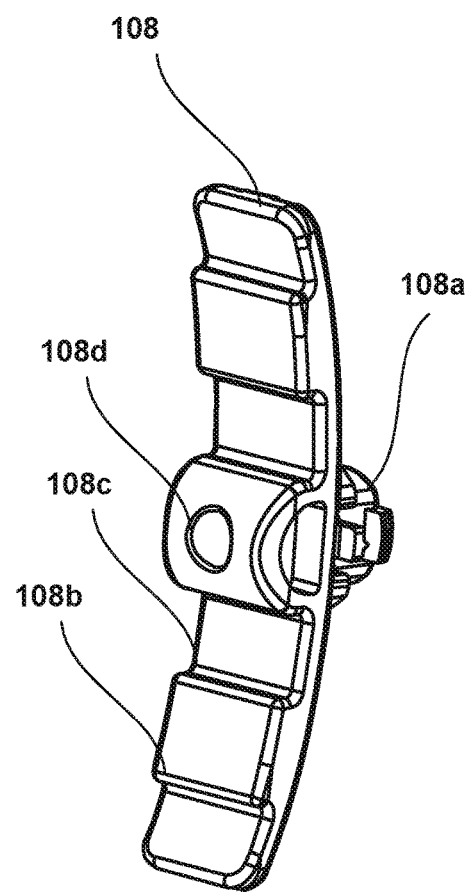
FIG. 6B is a diagram that illustrates a second perspective view of the bottom stabilizer of the incontinence clamping device, according to another exemplary embodiment of the present invention.

FIG. 6A is a diagram that illustrates a first perspective view of the bottom stabilizer 108 of the incontinence clamping device 100, according to another exemplary embodiment of the present invention. In FIG. 6A, the first perspective view of the bottom stabilizer 108 has been shown from outside showing an outer surface. FIG. 6B is a diagram that illustrates a second perspective view of the bottom stabilizer 108 of the incontinence clamping device 100, according to another exemplary embodiment of the present invention. In FIG. 6B, the second perspective view of the bottom stabilizer 106 has been shown from inside showing an inner surface. FIG. 6C is a diagram that illustrates a cross-sectional side view of the bottom stabilizer 108 of the incontinence clamping device 100, according to another exemplary embodiment of the present invention. The only difference in the bottom stabilizer 108 (of FIGS. 6A, 6B, and 6C) with respect to the bottom stabilizer 108 (of FIGS. 5A, 5B, and 5C) is that the bottom stabilizer 108 (of FIGS. 6A, 6B, and 6C) includes the central elevated portion that is like an oval shaped portion unlike the bottom stabilizer 108 (of FIGS. 5A, 5B, and 5C) that has the diamond or crown shaped portion.

Figures 7A, 7B:
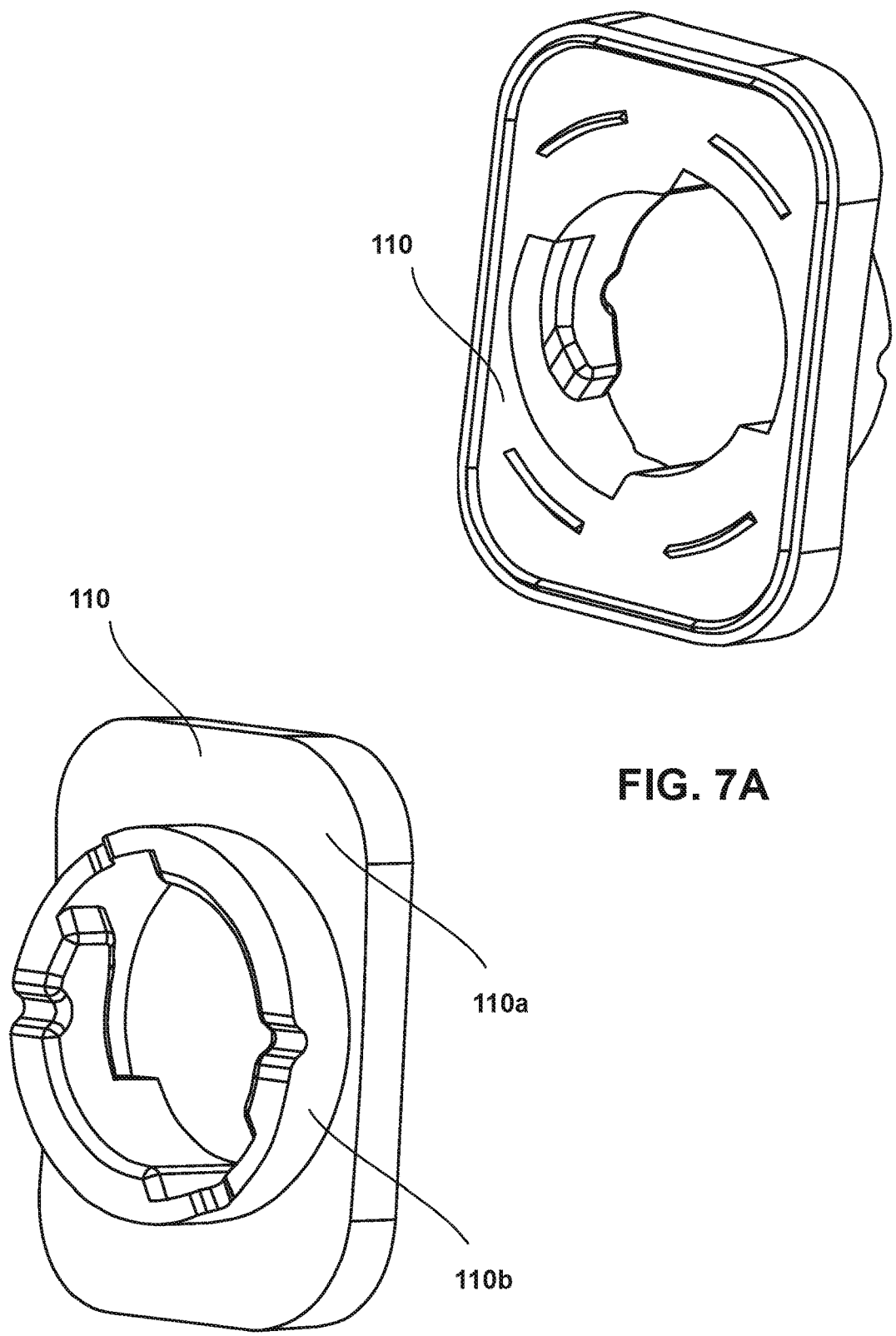
FIGS. 7A and 7B are diagrams that illustrate a perspective view of a lock ring of the incontinence clamping device, according to an exemplary embodiment of the present invention.

FIGS. 7A and 7B are diagrams that illustrate a perspective view of the lock ring 110 of the incontinence clamping device 100, according to an exemplary embodiment of the present invention. In an embodiment, the lock ring 110 is made up of a polycarbonate material.

In one embodiment, the lock ring 110 fits into the locking segment 102c from inside of the upper clamp arm 102. Further, the top stabilizer 106 may be configured to get locked with the lock ring 110 of the upper clamp arm 102. Here, for example, the lock 106a may be manually placed into the lock ring 110 of the upper clamp arm 102 and then may be manually rotated in one direction (for example, in a clockwise direction) to complete the locking of the lock 106a with the lock ring 110 of the upper clamp arm 102. Further, another lock ring 110 fits into the locking segment 104c from inside of the bottom clamp arm 104. The bottom stabilizer 108 may be configured to get locked with the lock ring 110 of the bottom clamp arm 104. Here, for example, the lock 108a may be manually placed into the lock ring 110 of the bottom clamp arm 104 and then may be manually rotated in one direction (for example, in a clockwise direction) to complete the locking of the lock 108a with the lock ring 110 of the bottom clamp arm 104.

In an embodiment, the lock ring 110 includes a flat surface 110a and a protruded portion 110b. The flat surface 110a has two sides, say a first side and a second side. The protruded portion 110b is like a hollow cylindrical such that there is circular gap in the lock ring 110. Further, the first side of the flat surface fits into the locking segment 102c or 104c from inside of the upper or bottom clamp arm 102 or 104. Further, the top or bottom stabilizer 106 or 108 may fit into the protruded portion 110b on the second surface of the lock ring 110 of the upper or bottom clamp arm 102 or 104.

Figure 8A:
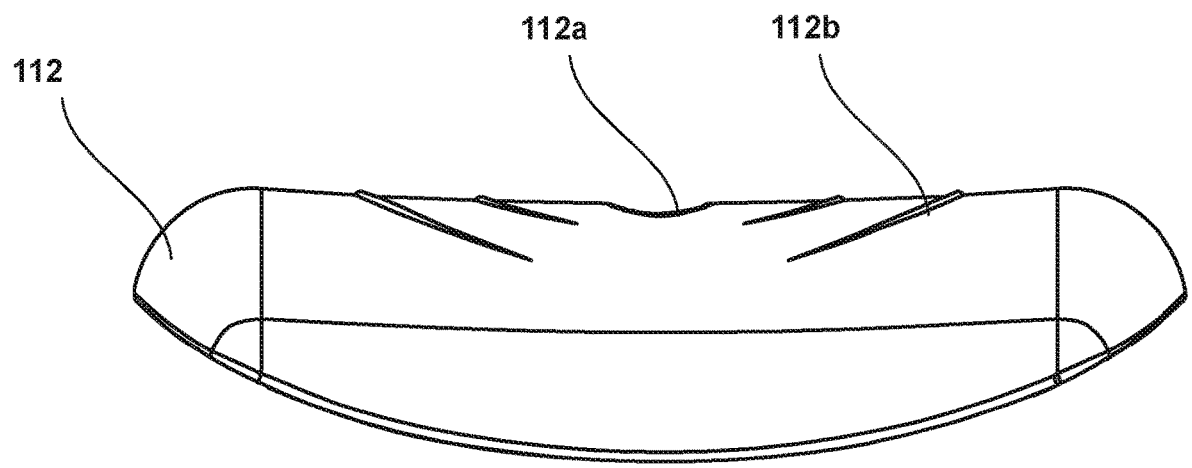
FIG. 8A is a diagram that illustrate a side view of an upper silicone fitting of the incontinence clamping device, according to an exemplary embodiment of the present invention.

FIG. 8A is a diagram that illustrate a side view of an upper silicone fitting 112 of the incontinence clamping device 100, according to an exemplary embodiment of the present invention. The upper silicone fitting 112 has two surfaces, say a lower portion that is semi-circular in shape and an upper portion that is a flat surface. The upper portion may include a protrusion (e.g., a bump) 112a that is facing inward. The upper portion may further include one or more linings 112b that are uniformly distributed on both sides of the protrusion 112a. Further, the lower portion may include a circular hole or gap that is located at its center.

Figure 8B:
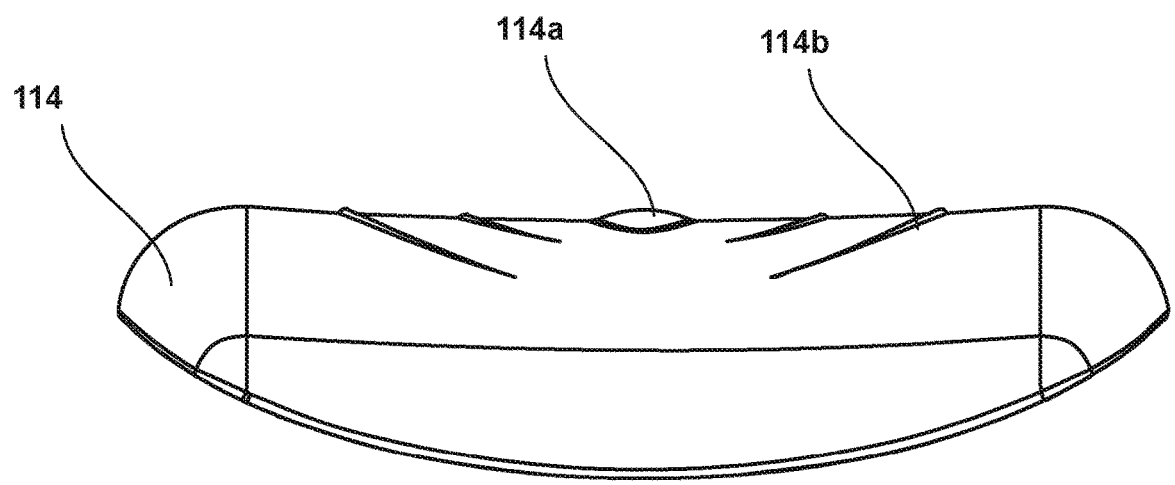
FIG. 8B is a diagram that illustrates a side view of a bottom silicone fitting of the incontinence clamping device, according to an exemplary embodiment of the present invention.

FIG. 8B is a diagram that illustrates a side view of a bottom silicone fitting 114 of the incontinence clamping device 100, according to an exemplary embodiment of the present invention. The bottom silicone fitting 114 has two surfaces, say a lower portion that is semi-circular in shape and an upper portion that is a flat surface. The upper portion may include a protrusion (e.g., a bump) 114a that is facing outward. The upper portion may further include one or more linings 114b that are uniformly distributed on both sides of the protrusion 114a. Further, the lower portion may include a circular hole or gap that is located at its center.

Figure 9:
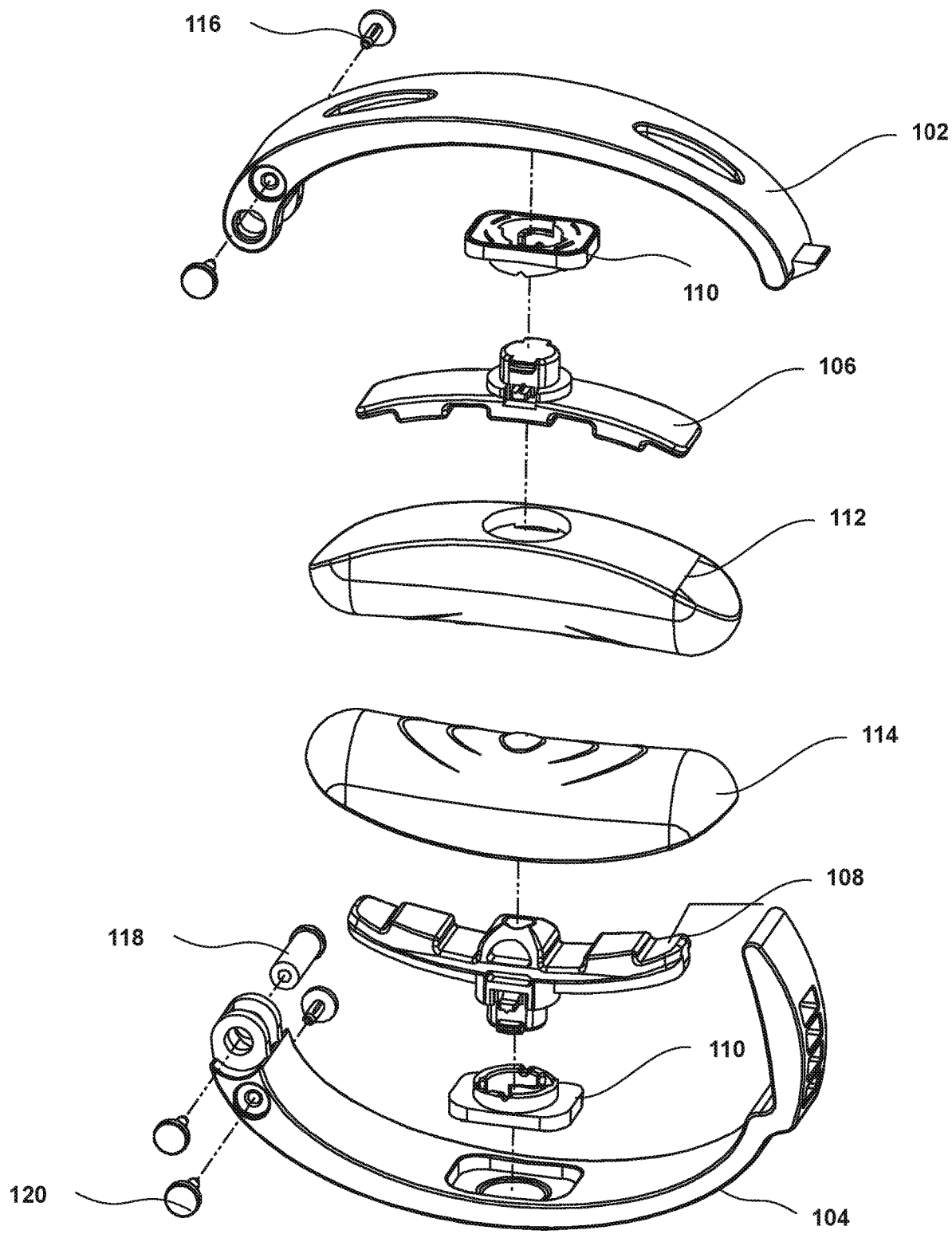
FIG. 9 is a diagram that illustrates a distributed arrangement of all components of the incontinence clamping device, according to an exemplary embodiment of the present invention.

FIG. 9 is a diagram that illustrates a distributed arrangement of all components of the incontinence clamping device 100, according to an exemplary embodiment of the present invention. The incontinence clamping device 100 includes the upper clamp arm 102, the bottom clamp arm 104, the top stabilizer 106, the bottom stabilizer 108, the lock ring 110, the upper silicone fitting 112, and the bottom silicone fitting 114. The upper lock ring 110 fits into the upper clamp arm 102. Further, the top stabilizer 106 is locked into the upper lock ring 110. The top stabilizer 106 is further fitted into the upper silicone fitting 112. Similarly, the bottom lock ring 110 fits into the bottom clamp arm 104. Further, the bottom stabilizer 108 is locked into the bottom lock ring 110. The bottom stabilizer 108 is further fitted into the bottom silicone fitting 114. Further, the upper clamp arm 102 and the bottom clamp arm 104 are attached to each other by means of one or more plastic plugs such as nut-bolt assemblies (as shown by 116, 118, and 120).

Figure 10:
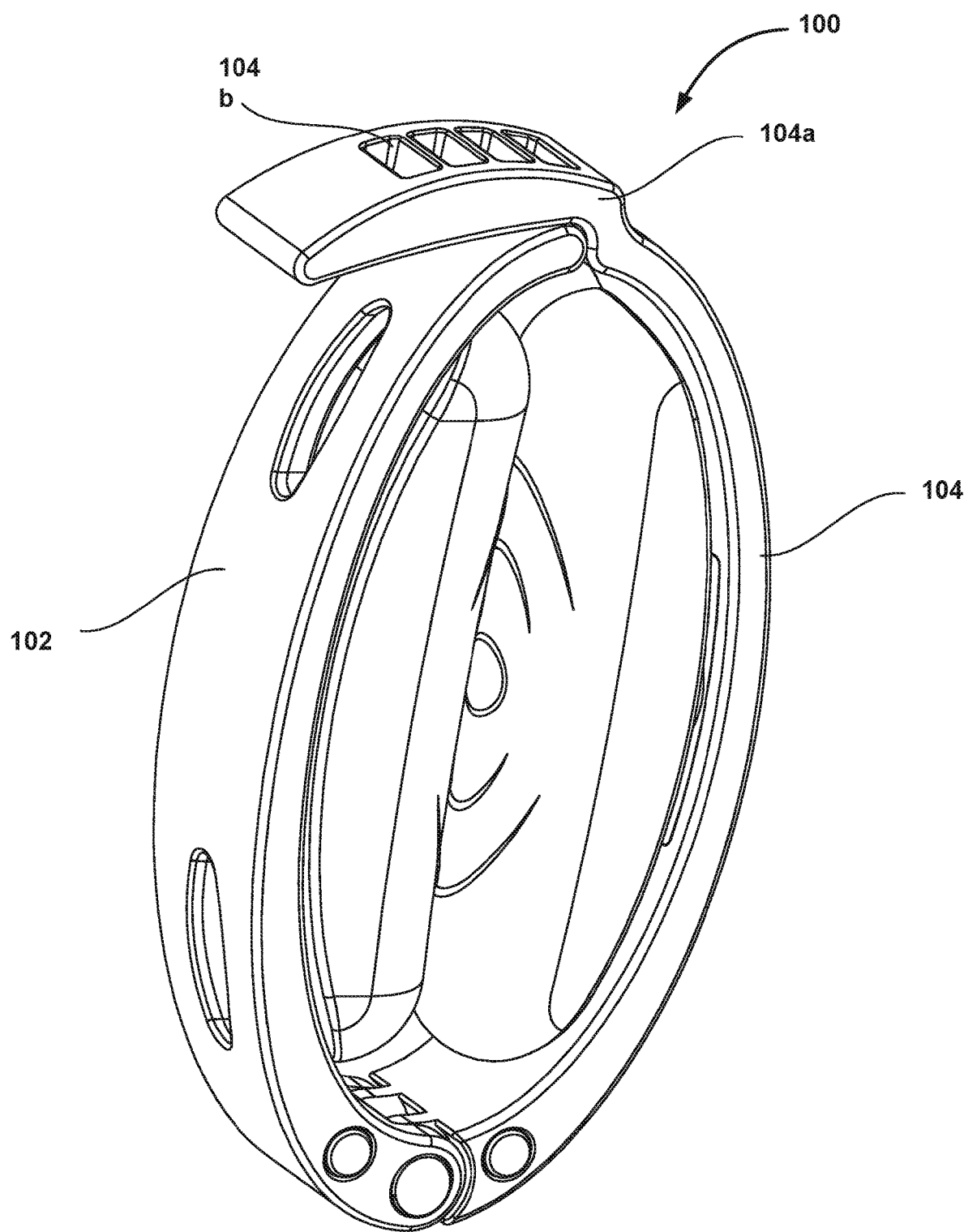
FIG. 10 is a diagram that illustrates a perspective view of the incontinence clamping device in a closed state, according to an exemplary embodiment of the present invention.
Figure 11:
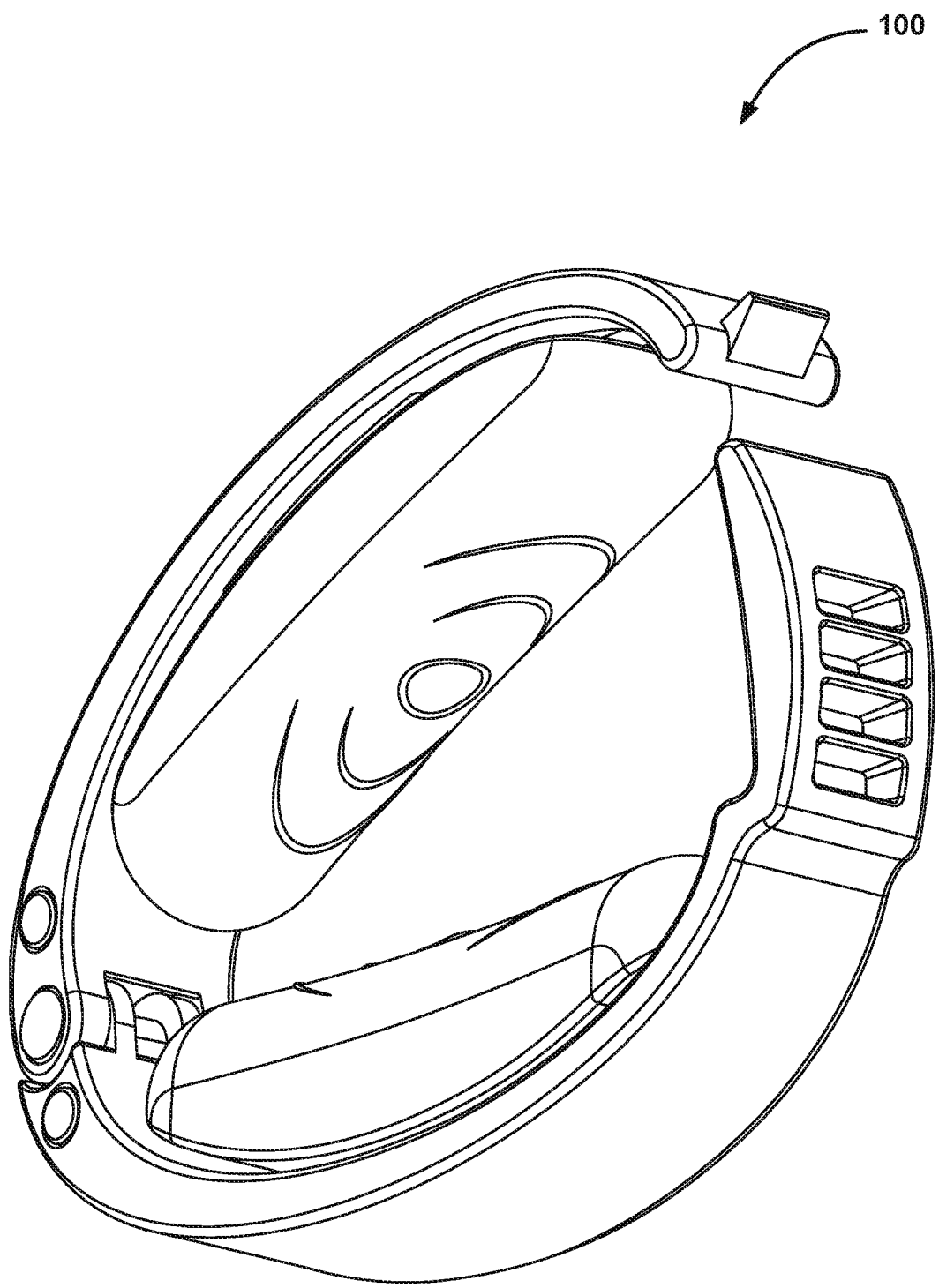
FIG. 11 is a diagram that illustrates a perspective view of the incontinence clamping device in an open state, according to an exemplary embodiment of the present invention.
Figure 12:
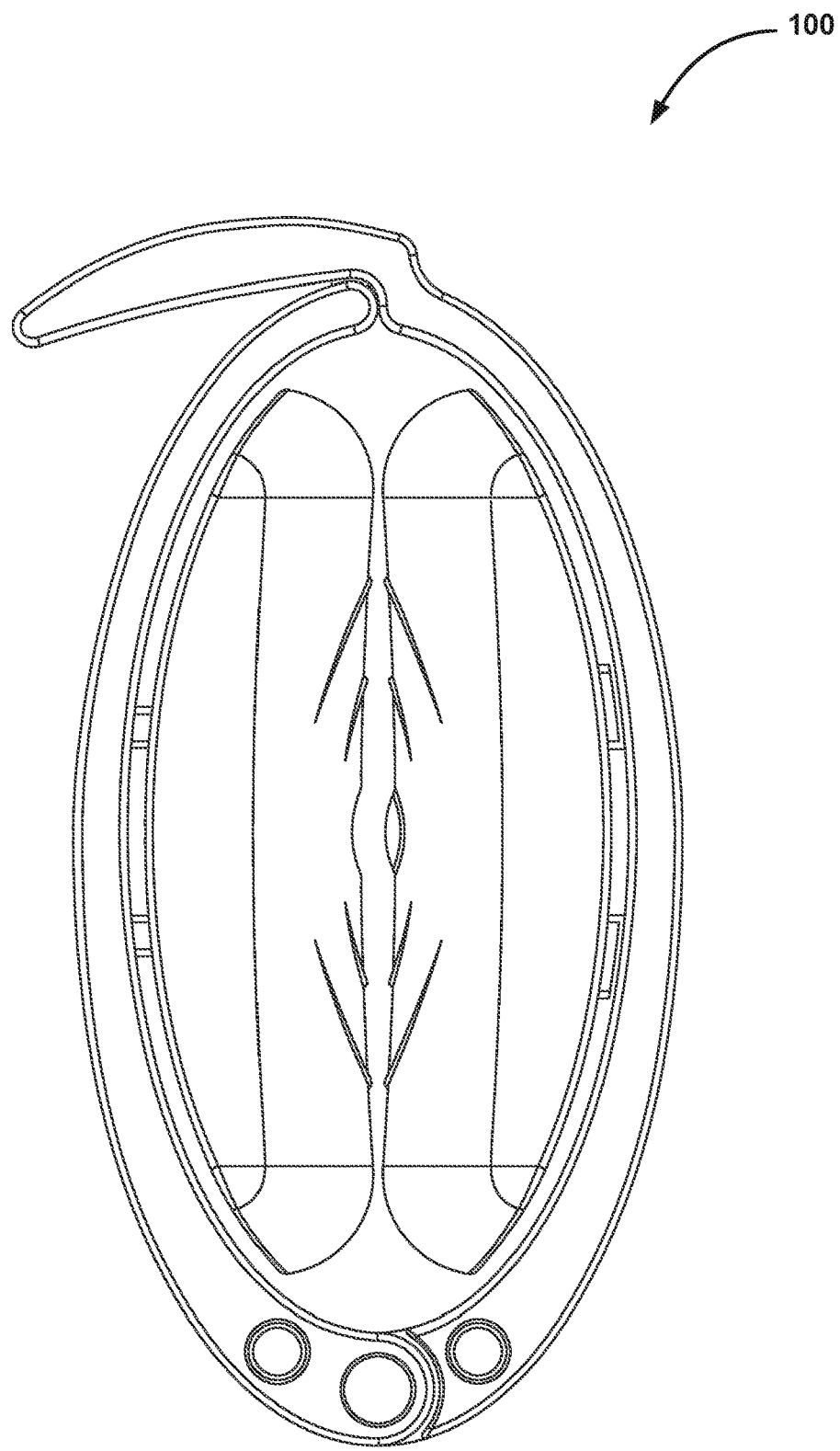
FIG. 12 is a diagram that illustrates a side view of the incontinence clamping device in its closed state, according to an exemplary embodiment of the present invention.

FIG. 10 is a diagram that illustrates a perspective view of the incontinence clamping device 100 in a closed state, according to an exemplary embodiment of the present invention. Here it is shown that the upper clamp arm 102 is removably attached to the bottom clamp arm 104 by means of the stopper 102a and the device locking component 104a. In an embodiment, the stopper 102a is inserted into one of the pluralities of interlocking gaps 104b to establish the locking of the upper clamp arm 102 with the bottom clamp arm 104. FIG. 11 is a diagram that illustrates a perspective view of the incontinence clamping device 100 in an open state, according to an exemplary embodiment of the present invention. In the open state, the upper clamp arm 102 is not attached to the bottom clamp arm 104 i.e., the stopper 102a is not inserted into any of the plurality of interlocking gaps 104b. FIG. 12 is a diagram that illustrates a side view of the incontinence clamping device 100 in its closed state, according to an exemplary embodiment of the present invention.

Figure 13:
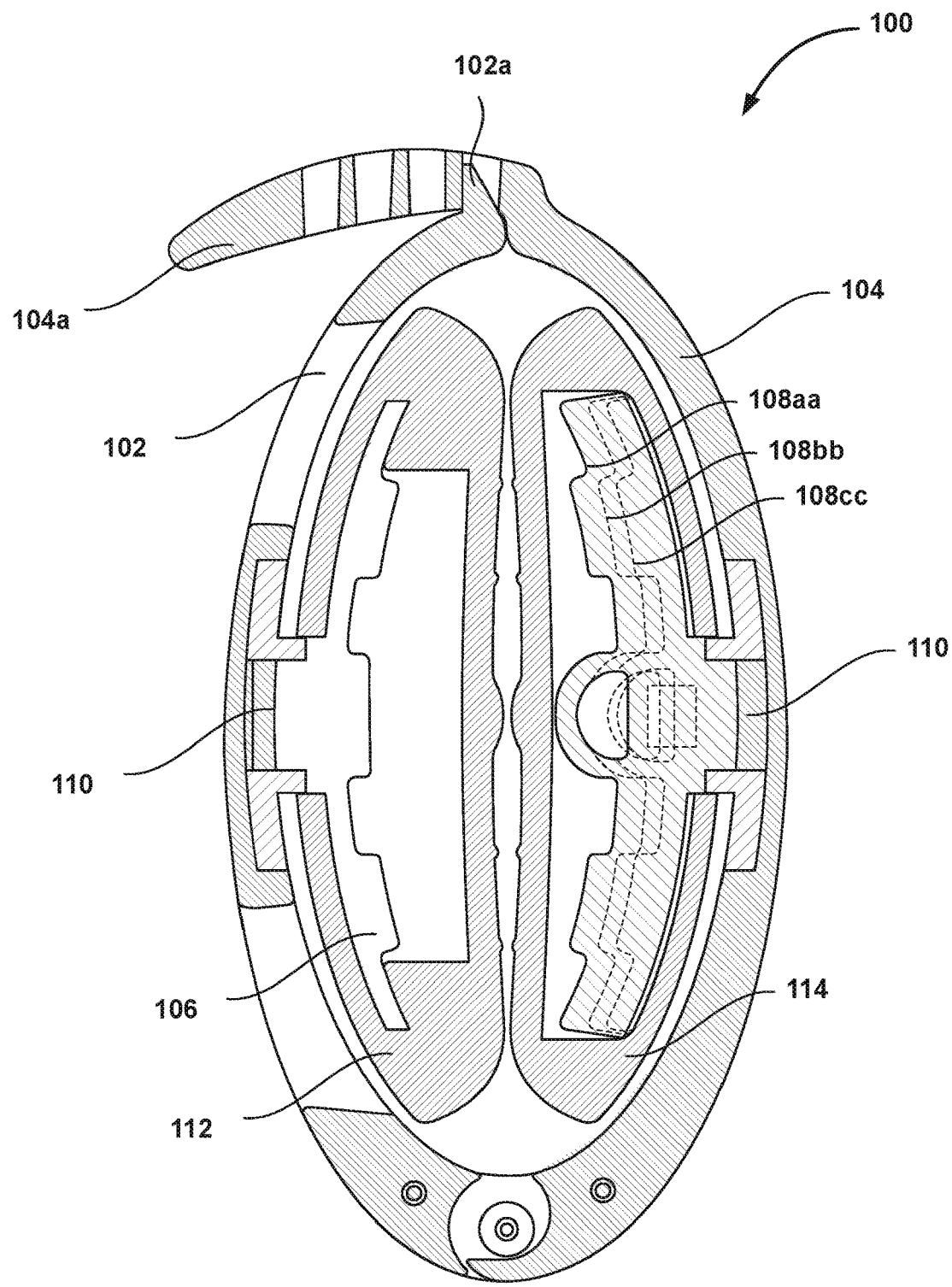
FIG. 13 is a diagram that illustrates a cross-sectional side view of the incontinence clamping device in its closed state, according to an exemplary embodiment of the present invention.

FIG. 13 is a diagram that illustrates a cross-sectional side view of the incontinence clamping device 100 in its closed state, according to an exemplary embodiment of the present invention. As shown, the top stabilizer 106 is attached to the lock ring 110. Similarly, the bottom stabilizer 108aa is attached to the lock ring 110. Alternatively, depending on the user's preferences such as the user's penis size, other variants of the bottom stabilizer 108bb or 108cc may be attached to the lock ring 110. These variants of the bottom stabilizer 108bb or 108cc may have a size that is different (smaller or larger) than the size of bottom stabilizer 108aa. Further, the top stabilizer 106 is inserted into the upper silicone fitting 112 as shown herein. Similarly, the bottom stabilizer 108aa, 108bb, or 108cc may be inserted into the bottom silicone fitting 114 as shown. Further, the upper clamp arm 102 is locked with the bottom clamp arm 104 by means of the stopper 102a and the device locking component 104a. In an embodiment, the stopper 102a is inserted into one of the pluralities of interlocking gaps 104b to establish the locking of the upper clamp arm 102 with the bottom clamp arm 104.

While various embodiments of the disclosure have been illustrated and described, it will be clear that the disclosure is not limited to these embodiments only. Numerous modifications, changes, variations, substitutions, and equivalents will be apparent to those skilled in the art, without departing from the spirit and scope of the disclosure, as described in the claims. Although particular embodiments of the invention have been described in detail for purposes of illustration, various modifications and enhancements may be made without departing from the spirit and scope of the invention. The scope of the invention is accordingly defined by the following claims.

What is claimed is:

1. An incontinence clamping device, comprising:
   an upper clamp arm having a stopper,
   a bottom clamp arm having a locking component with a plurality of interlocking gaps,
      wherein the stopper is operable to be inserted into one of the plurality of interlocking gaps for facilitating locking of the upper and bottom clamp arms,
   a top stabilizer having a plurality of zig-zag portion including at least one or more elevated and one or more non-elevated portions,
   a bottom stabilizer having a plurality of zig-zag portion including at least one or more elevated and one or more non-elevated portions,
   an upper silicone fitting that is used for accommodating the top stabilizer, and
   a bottom silicone fitting that is used for accommodating the bottom stabilizer,
      wherein the incontinence clamping device in its closed state allows for delivery of different pressures to urethra and corpus spongiosum as a function of various sizes of penises in a flaccid state.

2. An incontinence clamping device, comprising:
   an upper clamp arm;
   a bottom clamp arm;
   a top stabilizer;
   a bottom stabilizer having a plurality of zig-zag portions including at least one or more elevated and one or more non-elevated portions;
   an upper silicone fitting that is used in conjunction with the top stabilizer; and
   a bottom silicone fitting that is used in conjunction with the bottom stabilizer, wherein the incontinence clamping device in its closed state allows for delivery of different pressures to urethra and corpus spongiosum as a function of various sizes of penises in a flaccid state.

3. An incontinence clamping device, comprising:
   an upper clamp arm having an inside surface and an outside surface, the upper clamp arm comprising a plurality of gaps disposed from the inside surface to the outside surface such that, when the incontinence clamp device is unassembled, the plurality of gaps can be seen from both the inside surface and the outside surface;

a bottom clamp arm configured to lock with the upper clamp arm; and an upper silicone fitting disposed in assembled form about the inside surface of the upper clamp arm to obscure view of the plurality of gaps from the inside surface, wherein the incontinence clamping device in its closed state allows for delivery of different pressures to urethra and corpus spongiosum as a function of various sizes of penises in a flaccid state.

\* \* \* \* \*